(12) United States Patent
Costa et al.

(10) Patent No.: US 8,188,265 B2
(45) Date of Patent: May 29, 2012

(54) METHOD FOR THE ISOLATION OF MRNA FROM FORMALIN FIXED, PARAFFIN-EMBEDDED TISSUE

(75) Inventors: Rafael Rosell Costa, Badalona (ES); Miguel Tarón Roca, Badalona (ES)

(73) Assignee: Pangaea Biotech, S.A., Barcelona (ES)

( * ) Notice: Subject to any disclaimer, the term of this patent is extended or adjusted under 35 U.S.C. 154(b) by 64 days.

(21) Appl. No.: 12/090,767

(22) PCT Filed: Oct. 19, 2006

(86) PCT No.: PCT/EP2006/067591
§ 371 (c)(1),
(2), (4) Date: Jul. 7, 2008

(87) PCT Pub. No.: WO2007/045681
PCT Pub. Date: Apr. 26, 2007

(65) Prior Publication Data
US 2009/0264641 A1    Oct. 22, 2009

(30) Foreign Application Priority Data

Oct. 20, 2005 (EP) .................................. 05077417

(51) Int. Cl.
*C07H 21/02* (2006.01)
(52) U.S. Cl. ................................. 536/25.41; 536/25.42
(58) Field of Classification Search .................. None
See application file for complete search history.

(56) References Cited

U.S. PATENT DOCUMENTS

| | | | |
|---|---|---|---|
| 6,248,535 B1 | 6/2001 | Danenberg et al. | |
| 6,428,963 B2 | 8/2002 | Danenberg et al. | |
| 6,469,159 B1 | 10/2002 | Belly et al. | |
| 6,610,488 B2 | 8/2003 | Danenberg et al. | |

OTHER PUBLICATIONS (R) Chaw et al., "Isolation and Identification of Cross-Links from Formaldehyde-Treated Nucleic Acids," Biochemistry, 19(24), 5525-5531 (Nov. 1980).*

Abrahamsen, Helene Nortvig, et al., Towards Quantitative mRNA Analysis in Paraffin-Embedded Tissues Using Real-Time Reverse Transcriptase-Polymerase Chain Reaction, Journal of Molecular Diagnostics, Feb. 2003, pp. 34-41, vol. 5 No. 1.

Banerjee, S.K., et al, Microwave-Based DNA Extraction from Paraffin-Embedded Tissue for PCR Amplification, BioTechniques, 1995, pp. 768, 770, 772 and 773, vol. 18. No. 5.

Finke, J., et al., An Improved Strategy and a Useful Housekeeping Gene for RNA Analysis from Formalin-Fixed, Paraffin-Embedded Tissues by PCR, BioTechniques, 1993, pp. 448-453, vol. 14, No. 3.

Gruber, A.D., et al., Detection of bovine viral diarrhea virus RNA in formalin-fixed, paraffin-embedded brain tissue by nested polymerase chain reaction, Journal of Virological Methods, 1993, pp. 308-319, vol. 43.

Krafft, Amy E., Optimization of the Isolation and Amplification of RNA From Formalin-fixed, Paraffin-embedded Tissue: The Armed Forces Institute of Pathology Experience and Literature Review, Molecular Diagnosis, 1997, pp. 217-230, vol. 2, No. 3.

Masuda, Norikazu, et al., Analysis of chemical modification of RNA from formalin-fixed samples and optimization of molecular biology applications for such samples, Nucleic Acids Research, 1999, pp. 4436-4443, vol. 27, No. 22.

Specht, Katja, et al., Technical Advance, Quantitative Gene Expression Analysis in Microdissected Archival Formalin-Fixed and Paraffin-Embedded Tumor Tissue, American Journal of Pathology, Feb. 2001, pp. 419-429, vol. 158, No. 2.

Ambion Diagnostics, Optimum FFPE RNA Isolation Kit, Phenol-Free Isolation of Total RNA from Fixed Paraffin-Embedded Tissues Optimized for qRT-PCR, Ambion Diagnostics, Insert Version 2, 4 pages, published in Ambion TechNotes vol. 11, No. 2, Mar. 2004 [online] [retrieved on Oct. 19, 2011] Insert available at: www.asuragen.com/pdfs/optimum_manual.pdf.

* cited by examiner

*Primary Examiner* — Lawrence E Crane
(74) *Attorney, Agent, or Firm* — Andrew D. Gerschutz; Tristan A. Fuierer; Moore & Van Allen, PLLC

(57) ABSTRACT

Formalin fixation causes cross-linkage between nucleic acids and proteins and covalently modifies RNA. As a result, the molecules are rigid and may comprise subsequent RNA extraction. The invention provides a method for recovering RNA from formalin fixed paraffin-embedded tissue, including a short additional step of incubation with proteinase K after the first digestion step that makes a significant enhancement of the quality and quantity of the extracted RNA and subsequently, an improvement in the detection of gene expression is achieved. The method of the invention has the advantage of minimizing the number of manipulations, eliminating the need for potentially toxic solvents, and increasing significantly the amount of RNA recovered, and therefore the sensibility, when compared with previous methods.

10 Claims, No Drawings

METHOD FOR THE ISOLATION OF MRNA FROM FORMALIN FIXED, PARAFFIN-EMBEDDED TISSUE

CROSS-REFERENCE TO RELATED APPLICATIONS

This application is filed under the provisions of 35 U.S.C. §371 and claims the priority of International Patent Application No. PCT/EP2006/067591 filed on 19 Oct. 2006 entitled "Method for the Isolation of mRNA From Formalin Fixed, Paraffin-Embedded Tissue" in the name of Rosell Costa, Rafael et al., which in turn claims priority of Application No. 05077417.3 (EP) filed on 20 Oct. 2005, all copies of which are hereby incorporated by reference herein in their entirety.

FIELD OF THE INVENTION

The present invention relates to the isolation of mRNA from a formalin-fixed, paraffin-embedded biological tissue sample.

BACKGROUND

Quantitative determination of gene expression levels is a powerful approach for the comparative analysis of normal and neoplastic tissue. Gene expression profiling is increasingly important both in biological research and in clinical practice and has been used to, for example, classify various cancer types, and to predict clinical outcome of cancer, such as breast cancer and lung cancer.

Analysis of gene expression at the mRNA level is a central component of molecular profiling. Sensitive and specific methods for studying RNA derived from fresh tissues and cells are well described, and include techniques based on the use of reverse transcriptase-polymerase chain reaction (RT-PCR). Recent technological improvements, including the introduction of highly sensitive fluorescence-based real-time RT-PCR procedures, now allow for rapid and specific quantification of even small amounts of mRNA. However, the use of RT-PCR based methods to quantify mRNA in clinical specimens has been restricted by the limited availability of suitable fresh or frozen study tissues. In many situations where gene expression profiling is potentially useful, there is insufficient material for analysis. To allow conclusions regarding the clinical significance of the results obtained with such techniques, the examination of large numbers of pathological tissue specimens representing different disease stages and histological tumour types and grades is essential.

One possible answer to this problem may lie in the archives of formalin-fixed, paraffin-embedded (FFPE) tissue specimens which have been archived in quantity in pathology departments, along with their clinical histories and prognoses throughout the world. These collections already represent an invaluable research resource for studying the molecular basis of disease, making it possible to perform large retrospective studies correlating molecular features with therapeutic response and clinical outcome. Accordingly, formalin-fixed samples are attracting increasing attention as RNA sources. Archival formalin-fixed, paraffin-embedded (FFPE) tissue specimens, in conjunction with clinical data are the most widely available basis for such retrospective studies. The reliable quantification of gene expression in formalin-fixed, paraffin-embedded tissue, however, has been subject to serious limitations so far.

Techniques for extraction and analysis of DNA from FFPE tissues have been optimized allowing a range of molecular genetic studies to be performed on archival and routine diagnostic histopathological material. Although this is a lesser problem for DNA, RNA isolated from paraffin-embedded tissue blocks is of poor quality because extensive degradation of RNA can occur before completion of the formalin fixation process. Moreover, formalin fixation causes cross-linkage between nucleic acids and proteins and covalently modifies RNA by the addition of mono-methylol groups to the bases. As a result, the molecules are rigid and susceptible to mechanical shearing, and the cross-links may compromise subsequent RNA extraction, reverse transcription and quantification analysis. Therefore, in order to utilize FFPE tissues as a source for gene expression analysis, a reliable method is required for extraction of RNA from the cross-linked matrix.

Since Rupp (Rupp, G. M. and Locker, J., 1988) first reported northern hybridization of formalin-fixed samples, significant efforts have been made toward recovery of RNA from formalin-fixed tissues. Various modifications were made to the extraction steps, using RT-PCR to evaluate the outcome. In all reports, successful amplifications were limited to small fragments and sensitivities in transcript detection were much worse than with fresh material, although their alterations to the protocols did improve the results somewhat. The following three possibilities have been stated as the reasons for the poor results: RNA was degraded in the tissue before, during or after fixation; the RNA was resistant to extraction probably due to cross-linking with proteins; the extracted RNA from fixed specimens was chemically modified by formalin in a way that is still elusive. However, direct evidence for each of these possibilities and thoughtful investigation regarding the contribution of these three possibilities to the overall results has been lacking.

U.S. Pat. No. 6,248,535 discloses a method for the isolation of RNA from formalin-fixed, paraffin-embedded (FFPE) tissue specimens. In such method, the tissue sample is first deparaffinized and further homogenized in a solution comprising a chaotropic agent, like, for example, guanidinium isothiocyanate. The homogenate is thereafter heated at about 100° C. in a solution with a chaotropic agent. RNA is further recovered from the solution by, for example, phenol-chloroform extraction.

Krafft et al. (1997) *Molecular Diagnosis* vol. 2, no. 3, pages 217-230 describes the isolation and amplification of RNA from FFPE tissue. A process is described comprising a digestion with proteinase K, followed by alcohol precipitation and RT-PCR. Several concentrations of proteinase K were tested; optimal proteolytic digestion was obtained with high concentrations of proteinase K.

Masuda et al. (1999) *Nucleic Acid Research* vol. 27, no. 22, pages 4436-4443 describe several methods for the extraction of RNA from formalin fixed samples, finding that a proteinase K digestion at 45° C. for one hour, followed by precipitation with alcohol and a treatment with DNAse.

Spetch et al. (2001) *American Journal of Pathology* vol. 158, no. 2, pages 419-429 describes a procedure for the quantitative gene expression analysis in microdissected archived formalin-fixed and paraffin embedded tumour tissue trough RNA micro-scale extraction in conjunction with real-time quantitative reverse transcriptase-polymerase chain reaction.

Finke, J. et al (1993). *Biotechniques, Informa Life Sciences*, vol. 14, no. 3, pages 448-453 describes a strategy and a useful housekeeping gene for RNA analysis from formalin-fixed, paraffin-embedded tissues by PCR.

However, the above methods do not provide enough sensibility when small amounts of RNA are to be detected. More accurate and reliable techniques for the isolation of RNA from paraffin-embedded tissue are particularly needed for the study of gene expression in tumour tissues. The ability to routinely study mRNA expression in FFPE tumour tissues, even when only small amounts are present, would be an important advance, opening up the histopathology archive to molecular profiling and allowing analysis of gene expression at the RNA level in standard diagnostic specimens and allowing establishing good correlations between gene expression and the clinical outcome.

SUMMARY OF THE INVENTION

In one aspect the present invention provides a reliable method for recovering RNA from a formalin-fixed, paraffin-embedded biological tissue sample comprising:
a) deparaffinizing the sample,
b) contacting said sample with a solution comprising an effective concentration of proteinase K and heating the sample in said solution to a temperature in the range of about 30 to about 60° C., for a time period of about 12 to 20 hours,
c) adding an effective concentration of proteinase K to the solution obtained from b) for a time period of about 5 to about 30 minutes at a temperature range of about 40 to about 75° C., and
d) recovering said RNA from said solution.

The method of the invention has the advantage of minimizing the number of manipulations, eliminating the need for potentially toxic solvents, and increasing significantly the amount of RNA recovered, and therefore the sensibility, when compared with previous methods.

DETAILED DESCRIPTION OF THE INVENTION

In order to facilitate the understanding of the present description, the meaning of some terms and expressions in the context of the invention will be explained below:

The term "RNA" refers to ribonucleic acid. An RNA sequence is a ribonucleotide sequence.

The term "mRNA" refers to messenger ribonucleic acid, which is the fraction of total RNA which is translated into proteins.

The term "cDNA" refers to a nucleotide sequence complementary of a mRNA sequence.

The term "formalin-fixed, paraffin-embedded biological tissue sample" (FFPE) refers to a tissue sample obtained from a tissue which has been previously fixed in a formalin solution and afterwards embedded in paraffin. While frozen tumour tissue is not widely available, paraffin blocks are routinely prepared from every type of tissue, such as, for example, a tumour tissue, after surgery, allowing large-scale retrospective investigations.

Pathological specimens are routinely taken from patients for use in disease diagnosis and the study of disease marker patterns. Teaching hospitals, medical schools and universities have stores containing millions of such samples, some of which date back over 30 years. These samples represent a major and, at present, an under-used resource for the study of disease progression, the detection of viral, bacterial or parasitic organisms, DNA abnormalities or the detection of genetic diseases. Many pathological specimens, for example archival blocks and pathological slides, are chemically fixed to retain the tissue architecture and especially the conformation of the proteins in situ. The use of formalin fixation and paraffin embedding to fix and preserve tissue samples taken from biopsies, resections and smears is almost universal. Whilst the fixatives commonly used effectively preserve the structure of the proteins, the extraction of nucleic acids and in particular RNA from the specimens can be difficult. The process of the invention improves such extraction and can be applied to any tissue sample from a wide range of tumour types and to an unlimited range of target genes.

RNA extraction from archival paraffin-embedded pathology tissue samples is particularly useful in retrospective studies in which the determination of a molecular diagnosis can be correlated with patient outcome, in particular providing the possibility of correlating the presence or absence of a particular disease, morphological diagnosis or type, disease stage, prognosis, and response to treatment, where the clinical outcome is already known. This will have implications for the future preparation of individual tumour "gene expression profiles" whereby expression levels could be determined in individual patient samples for a range of genes that are known to influence clinical outcome and response to various chemotherapeutic agents, and then tailor chemotherapy to that profile. The presence of polymorphisms, mutations or deletions can also be investigated with the method of the present invention.

Examples of tissues from which nucleic acids can be extracted using the present invention include, but are not limited to, both normal and cancerous lung tissue, colon tissue, pancreatic tissue, breast tissue, prostate tissue, blood and other body fluids or cellular material containing nucleic acids that can be detected.

RNA isolated by the method of the invention is suitable for a number of applications in molecular biology including reverse transcription. Purified RNA can be used to determine the level of gene expression in a formalin-fixed, paraffin-embedded biological tissue sample by reverse transcription, polymerase chain reaction (RT-PCR) amplification. Using appropriate PCR primers the expression level of any messenger RNA can be determined by the method of the invention.

In the following, details are given of each step of the process.

Deparaffinization of Samples

Biological samples are often fixed with a fixative. Preferably the samples of the invention are fixated with formalin, although other fixatives can be envisaged as well. In fact, aldehyde fixatives such as formalin (formaldehyde) and glutaraldehyde are typically used. Other techniques of inducing fixation well known for the skilled person in the art can include, but are not limited to, alcohol immersion or other fixation solutions. The samples used for the method of the present invention are embedded in paraffin and archived for ulterior analysis.

In the deparaffinization step the bulk of paraffin is removed from the paraffin-embedded sample. The preferred techniques of the invention utilize direct melting for deparaffinization, avoiding the use of organic solvents which can degrade the sample and damage the environment. It also has the advantage of reducing the number of manipulations and possibility of degradation or contamination of the RNA. The temperature used for direct meting is in the range of 50-65° C., preferably about 55° C. High temperatures should be avoided; otherwise the sample can be degraded.

However, a number of other techniques for deparaffinization are well known for any person skilled in the art and can include, but are not limited to, washing with an organic solvent such as benzene, toluene, ethylbenzene, xylenes, and mixtures thereof. Any suitable technique can be used with the present invention.

Digestion with Proteinase K Solution

As previously explained formalin fixation causes cross-linkage between nucleic acids and proteins and covalently modifies RNA by the addition of mono-methylol groups to the bases. As a result, the molecules are rigid and susceptible to mechanical shearing, and the cross-links may compromise subsequent RNA extraction, reverse transcription and quantification analysis.

Therefore, in the method of the invention proteinase K is used as a protease enzyme capable to break down tissues and proteins helping to release the nucleic acids. The protease may also degrade nucleases making the released RNA more stable.

Thus, after deparaffinization, the samples are contacted with a solution comprising an effective concentration of proteinase K, and subsequently digested in a digestion solution at a temperature of about 30° C. to about 60° C., for a time period of about 12 to about 20 hours. The protease enzyme serves to produce at least a partial tissue break down such that nucleic acids are released. In a preferred embodiment, the time period is of about 16 hours.

Proteinase K (E. C. 3.4. 21.64 from Tritirachium album) is commercially available as a lyophilized powder or in aqueous solutions or suspension (Sigma-Aldrich, St. Louis, Mo.). The concentrations of proteinase K in the extraction composition is preferably at least about 25 μg/ml or greater, at least about 100 μg/ml or greater, or at least about 200 μg/ml or greater. An amount of about 500 μg/ml is most preferred. The extraction composition of the present invention is typically an aqueous solution, however, in certain embodiments, the extraction composition can be in the form of an aqueous dispersion, suspension, emulsion or the like.

The aqueous portion of the extraction composition is at an alkaline pH of about 7.5 or greater. Preferably, the extraction composition pH is about 8.0. The pH is achieved using a buffer. Any of a number of buffering agents can be used in the extraction composition, the selection and use of which can be readily performed by the skilled artisan (see for example Beynon and Esterby, Buffer Solutions: The basics, BIOS Scientific Publishers, Oxford, 1996). The amount of buffer used is dependent upon the pKa and is that sufficient to maintain the desired pH. Useful buffers include, but are not limited to, 3-(N-morpholino)propanesulfonic acid, 3-(N-morpholino)ethanesulfonic acid, tricine, glycine, TRIS, phosphate, and others readily apparent to those skilled in the art.

Surfactants, such as sodium dodecyl sulphate, can also be used in the digestion solution. If present, preferably low amounts are used.

A $Ca^{2+}$ chelator, such as EDTA, may be used to complex the ions which interfere with the activity of the tissue digestion enzyme. If present in the extraction composition, is at a concentration of about 100 mM or less, preferably at a concentration of about 50 mM or less, preferably at a concentration of about 10 mM or less, preferably at a concentration of about 1 mM or less.

The sample is contacted for a time period of about 12 to 20 hours with the proteinase K solution and the digestion buffer under conditions sufficient to release the RNA.

In a preferred embodiment, and in order to improve the quality of the extracted RNA, the temperature range of the heating step for recovering RNA is from about 40 to about 60° C., preferably from about 50-55° C. Higher temperatures can inactivate the enzyme and degrade the RNA.

In order to increase the quality of the RNA to be extracted, an additional step of incubation with proteinase K is used in the method of the present invention. Contrary to the teaching of the prior art, where normally after the digestion a heating step is used to inactivate the enzyme left, in the present invention fresh enzyme is added to the solution and a short digestion step is carried out. It has been found that this additional short digestion dramatically improves the amount of RNA extracted.

Other prior art documents (Finke, J. et al cited supra) describe RNA isolation procedures from FFPE wherein additional incubation steps with proteinase K are carried out. However, such procedures are long, up to 60 hours, and thus, fresh proteinase K is added every 24 hours during the incubation with the digestion buffer until the tissue is completed digested.

The inventors have now discovered that a short additional step of incubation with proteinase K after the first digestion step makes a significant enhancement of the quality and quantity of the extracted RNA and subsequently, an improvement in the detection of gene expression is achieved (see Example 2).

Thus, an effective concentration of proteinase K is added to the previous solution for an extra time period of about 5 to about 30 minutes at a temperature range of about 40 to about 75° C. The inventors have found that this last proteinase K step is essential for the proper solubilization of the tissue and recovery of good quality RNA. Indeed, proteinase K added at that moment completely solubilizes the tissue and enables a very efficient extraction of the nucleic acid.

RNA Recovery

The method of the invention further comprises recovering said RNA from the solution. In a particular embodiment, the RNA is recovered by extraction from said solution with a water insoluble organic solvent. In a preferred embodiment, said water insoluble organic solvent comprises chloroform. Preferably a phenol/chloroform mixture is used.

In another particular embodiment, said RNA is further purified by ethanol precipitation. RNA extraction protocols are well known by a person skilled in the art, see for example Chomczynski P. et al., Anal. Biochem., 1987, 162: 156; Chomczynski P., Biotechniques, 1993, 15: 532.

As shown in the examples of the present invention, if necessary a DNAse treatment can be carried out after RNA purification. In some cases RNA isolated from tissues or cells is contaminated with trace amounts of genomic DNA that can be detectable by PCR (Polymerase Chain Reaction). Thus, is order to improve the quality of the RNA extracted with the method of the present invention, contaminating DNA may be eliminated by DNAse treatment. DNAse is added to the extracted RNA and is incubated at 37° C. for a time period of, for example, 30 minutes.

Alternatively, RT-PCR amplification can be done using primers that will not amplify the DNA, for example selecting an area that overlaps over two exons. In such cases, the DNAse treatment can be avoided, further preserving the quality of the RNA.

RNA Amplification and Quantification

The total RNA extract obtained represents the working material for the next step. The RNA extracted from tissue samples according to the present invention is suitable for subsequent amplification. The general principles and conditions for amplification and detection of nucleic acids, such as using PCR, are well known for the skilled person in the art and described in the references cited in the background art.

Once the sample has been obtained and the total RNA has been extracted, the quantification of the level of the mRNA can be carried out by quantifying the level of mRNA or the level of the corresponding cDNA of the mRNA.

Amplified nucleic acids can be detected in a number of known ways, such as those described in U.S. Pat. No. 4,965,188 (Gelfand et al.). For example, the amplified nucleic acids can be detected using Southern blotting, dot blot techniques, or nonisotopic oligonucleotide capture detection with a labelled probe. Alternatively, amplification can be carried out using primers that are appropriately labelled, and the amplified primer extension products can be detected using procedures and equipment for detection of the label.

In an example, detection and quantification of mRNA is carried out by blotting the mRNA onto a nylon membrane by means of blotting techniques, such as, for example, Northern blot, and detecting it with specific probes of the specific mRNA or of its cDNA.

In another example, the quantification of the mRNA can be achieved by a two-step method comprising a first step of amplification of the RNA, preferably mRNA, or amplification of the cDNA synthesized by reverse transcription (RT) from the mRNA, and a second step of quantification of the amplification product of the mRNA or its corresponding cDNA. One example of mRNA amplification consists in reverse transcribing the mRNA into cDNA, followed by the Polymerase Chain Reaction (PCR) using the appropriate oligonucleotide primers (U.S. Pat. No. 4,683,195, U.S. Pat. No. 4,683,202 and U.S. Pat. No. 4,965,188). Many methods for detecting and quantifying the PCR amplification products have been previously disclosed, any of which methods could be used in this invention. In a particular embodiment, the amplification and quantification of the mRNA is carried out by means of real time quantitative RT-PCR (Q-PCR) and subsequent hybridization with a probe specific for the gene of interest, optionally said probe being labelled with an appropriate tag, as for example a radioactively labelled probe (e.g., radioactive, chemiluminescent, or fluorescent tags such as fluorescein, Cye3-dUTP, or Cye5-dUTP), hybridizing target genes to the probes, and evaluating target-probe hybridization. A probe with a nucleic acid sequence that perfectly matches the target sequence will, in general, result in detection of a stronger reporter-molecule signal than will probes with less perfect matches.

Probes to be used are specific for the mRNA of interest or its cDNA. Said probes can be easily designed by the skilled person in the art in view of the nucleotide sequence of the gene of interest by using any suitable software. According to the invention, probes are selected from the group of nucleic acids including, but not limited to, DNA, genomic DNA (gDNA), cDNA and oligonucleotides; and may be natural or synthetic. Oligonucleotide probes preferably are 20 to 25-mer oligonucleotides whereas DNA/cDNA probes preferably are 500 to 5,000 bases in length; nevertheless, in both cases, other lengths may be used.

The final step of the method consists in comparing the level (amount or concentration) of mRNA of interest or the level of its cDNA determined in a sample from the subject under analysis, with the level of mRNA of interest or with the level of its cDNA determined in control samples, such as samples from control subjects, i.e., samples from healthy subjects or in previous samples from the same subject. Any conventional method can be used within the framework of the invention, as long as the in vitro measurement of the specific gene transcribed mRNA or its complementary cDNA can be performed in samples taken from the subjects to be analyzed (test samples) and from control samples.

The invention is further illustrated with the following Examples. They are provided to illustrate certain embodiments of the present invention, and are not to be construed as limiting the invention.

Example 1 mRNA Extraction and Analysis from Microdissected Formalin Fixed, Paraffin-Embedded Tissue 1. Materials and Methods
1.1. PEN (Polyethylene-Nafthalate PALM Cat n°: 1440-1000) membranes pretreatment.

Wash the slides by dipping them for 5 minutes into a coupling container of RNAse ZAP (Ambion Cat n°: 9870).

Wash the slides twice (5 minutes each time) with bi-distilled water and leave them to air dry.

Expose the dried slides to 234 nm wave length Uv lamp for 30 minutes.

Dip the slides into 0.1% Poly-L-lysine (Sigma Cat n°: P8920) coupling container.

Leave to air dry.
1.2. Sectioning

The tissue sections are then cut at 5 µm of thickness and placed into the oven for one hour at 55° C. Each slide must be stained using the Hematoxylin & Eosin procedure and checked under the microscope in order to select the optimal area to microdissect.

Once this process is completed, the samples should not be stored for a long time before RNA extraction. In the case of delayed storage, the following procedure is recommended:

Deparaffinizaton at 55° C. for one hour in an oven.
Dip it into the fused liquid paraffin for 15 minutes.
Leave at room temperature or at 4° C. for 15 minutes.
1.3. Staining

| | |
|---|---|
| Xylene × 2 | 5 minutes (each one) |
| Absolute ethanol × 1 Merck Cat n°: 1.00986.2500 | 1 minute 30 seconds |
| 95% Ethanol × 1 | 30 seconds |
| 70% Ethanol × 1 | 30 seconds |
| Bi-distilled Water | 1 minute |
| 1:3 diluted Harrison's Hematoxylin | 30 seconds |
| Bi-distilled water | 1 minute |
| 1 × Automation Buffer (Biomeda) | 1 minute |
| Bi-distilled water | 1 minute |
| 1:3 diluted Eosin Yellow | 1 minute |
| 95% Ethanol × 3 | 30 seconds |
| Absolute Ethanol × 1 | 30 seconds |
| Xylene × 1 | 5 minutes |
| Air dry | At least 30 minutes |

1.4. Microdissection

Before beginning the Laser Capture Microdissection, electrical charge must removed from every slide, by touching each one with a piece of metal a couple of times. If this step is skipped, then the fragment of microdissected tissue will remain on the slide after catapulting, making it nearly impossible to recover.
1.5. RNA Extraction Procedure The minimal amount of tissue needed for mRNA expression analysis is approximately 4 mm$^2$.

The microdissected tissue is collected in a 0.5 ml. cap tube with 2 µl of digestion buffer (10 mM Tris HCl pH 8.0, 0.1 mM EDTA pH 8.0, 2% SDS and 500 µg/ml of proteinase K).

After catapulting, add 195 µl of digestion buffer to the tube and cap it with the cap containing the microdissected tissue. Vortex and centrifuge for 5 minutes at 13000 rpm.

Trespass the resuspended pellet into a new 1.5 ml. tube.

Incubate at 60° C. for 16 hours in the thermoshaker at 850 rpm.

Add 10 µl of 20 mg/ml proteinase K.

Incubate for 15 minutes at 60° C.

Prepare the phenol solution on ice (500 μl of saturated water phenol GIBCO BRL: 15594-047+100 μl of chloroform (Merck Cat n°: 1.024451000)+2 μl of isoamilic alcohol Sigma Cat n°: I-9392).

Add one volume of phenol solution (approx. 210 μl) to the digested product.

Vortex and place on ice for 10 minutes.

Centrifuge at 12600 rpm for 10 minutes at 4° C.

Trespass the upper aqueous phase into a new 1.5 ml. tube.

Add 0.1 volume of sodium acetate (Applied Biosystems Cat n°: 4331560) and 2.5 μl Glycogen (20 mg/ml) (Roche Cat n°: 0901393).

Vortex for 30 seconds.

Add 1 volume of 2-propanol and vortex again.

Leave for 30 minutes at −20° C.

Centrifuge at 12600 rpm for 10 minutes at 4° C.

Remove the supernatant and add 150 μl of 70% Ethanol.

Centrifuge at 12600 rpm for 5 minutes.

Remove the supernatant and leave to air dry.

Resuspend in 20-50 μl of Diethylpyrocarbonate (DEPC) water.

Incubate 65° C. for 5 minutes.

1.6. DNAse Treatment

Use 10 μl of RNA and add 1 μl of DNAse (DNA-free AMBION Cat n°: 1906) and 1.2 μl of 10× DNAse buffer.

Incubate at 37° C. for 30 minutes.

Add 0.1 volume of DNAse inactivation reagent to the digestion product.

Centrifuge at 14000 rpm for 1 minute.

Trespass the supernatant into a new tube.

1.7. Retrotranscription

Use 9.4 μl of DNAse-treated RNA.

Add 2 μl of RT mix 1 (250 ng/μl Random primer ROCHE Cat n°: 48190-011+1 μl of 10 mM dNTP's Roche Cat n°: 1.814.362).

Denature the RNA at 65° C. for 5 minutes.

Immediately chill on ice.

Add 6 μl of RT mix 2 (4 μl of 5×RT buffer and 2 μl of 0.1 M DTT)+1 μl of RNA guard (Amersham Pharmacia Cat n°: 27-0815-01)

Incubate the samples at 25° C. for 10 minutes.

Bring the samples up to 37° C. and add 1 μl of MMLV (Moloney Murine Leukemia Virus Reverse transcriptase) (200 units) and incubate for 45 minutes.

Inactivate MMLV by heating it at 70° C. for 10 minutes.

The cDNA is now ready for use or can be stored at −20° C.

Example 2

Following the protocol described in example 1, several samples were subjected to the RNA extraction method of the invention. For control the same samples were subjected to the same protocol but omitting the second addition of proteinase K. After amplification and quantification as described, the following results were, as given in the following table:

| Effect of Proteinase K on RNA extraction from FFPE tissues | | | |
|---|---|---|---|
| Sample n° | +/−additional Proteinase K | Ct beta-actine in the RT-QPCR | x times more expression |
| 1 | +Prot K | 21.70 | 48.69 |
|   | −Prot K | 27.31 | 1 |
| 2 | +Prot K | 21.59 | 21.22 |
|   | −Prot K | 26.00 | 1 |
| 3 | +Prot K | 20.90 | 530.26 |
|   | −Prot K | 29.95 | 1 |
| 4 | +Prot K | 22.19 | 18.66 |
|   | −Prot K | 26.41 | 1 |
| 5 | +Prot K | 24.14 | 2.77 |
|   | −Prot K | 25.61 | 1 |

The results clearly show the significant improvement of the further addition of proteinase K and short digestion following the first step of digestion.

The invention claimed is:

1. A method for recovering formaldehyde-modified RNA from a formalin-fixed, paraffin-embedded biological tissue sample comprising:
   a) deparaffinizing the sample as known in the art,
   b) contacting said sample with a solution comprising an effective concentration of proteinase K and heating the sample in said solution to a temperature in the range of about 30 to about 60° C., for a time period of about 12 to 20 hours,
   c) adding an effective concentration of proteinase K to the solution obtained from b) for a time period of about 5 to about 30 minutes at a temperature range of about 40 to about 75° C.,
   d) recovering said formaldehyde-modified RNA as known in the art, and
   e) purifying said formaldehyde-modified RNA, wherein said formaldehyde-modified RNA is purified by ethanol precipitation.

2. The method of claim 1 wherein the temperature range of the heating in step b) is from about 45° C. to about 60° C.

3. The method of claim 1 wherein said formaldehyde-modified RNA is recovered in d) by extraction from said solution with a water insoluble organic solvent, wherein said water insoluble organic solvent comprises chloroform.

4. The method of claim 1 wherein the step a) of deparaffinizing the sample is accomplished by direct melting.

5. The method of claim 1, wherein the temperature range of the heating in step b) is from about 50° C. to about 55° C.

6. A method for recovering formaldehyde-modified RNA from a formalin-fixed, paraffin-embedded biological tissue sample comprising:
   a) deparaffinizing the sample by direct melting,
   b) contacting said sample with a solution comprising an effective concentration of proteinase K and heating the sample in said solution to a temperature in the range of about 30 to about 60° C., for a time period of about 12 to 20 hours,
   c) adding an effective concentration of proteinase K to the solution obtained from b) for a time period of about 5 to about 30 minutes at a temperature range of about 40 to about 75° C., and
   d) recovering said formaldehyde-modified RNA from said solution as known in the art.

7. The method of claim 6 wherein the temperature range of the heating in step b) is from about 45° C. to about 60° C.

8. The method of claim 6 wherein said formaldehyde-modified RNA is recovered in d) by extraction from said solution with a water insoluble organic solvent, wherein said water insoluble organic solvent comprises chloroform.

9. The method of claim 6 further comprising purifying said formaldehyde-modified RNA, wherein said formaldehyde-modified RNA is purified by ethanol precipitation.

10. The method of claim 6, wherein the temperature range of the heating in step b) is from about 50° C. to about 55° C.

* * * * *